(12) United States Patent
Akita

(10) Patent No.: US 7,367,672 B2
(45) Date of Patent: May 6, 2008

(54) OPHTHALMIC OBSERVATION APPARATUS

(75) Inventor: Junichi Akita, Nukata-gun (JP)

(73) Assignee: Nidek Co., Ltd., Gamagori-shi (JP)

( * ) Notice: Subject to any disclaimer, the term of this patent is extended or adjusted under 35 U.S.C. 154(b) by 160 days.

(21) Appl. No.: 11/473,125

(22) Filed: Jun. 23, 2006

(65) Prior Publication Data
US 2007/0010313 A1    Jan. 11, 2007

(30) Foreign Application Priority Data
Jul. 8, 2005    (JP)    ............................. 2005-199525

(51) Int. Cl.
*A61B 3/14*    (2006.01)
(52) U.S. Cl. ...................................... 351/206; 351/208
(58) Field of Classification Search ................ 351/206, 351/208, 214, 216–218
See application file for complete search history.

(56) References Cited

U.S. PATENT DOCUMENTS

| 5,177,511 A | 1/1993 | Feuerstein et al. ........... 351/205 |
|---|---|---|
| 5,396,302 A | 3/1995 | Triller et al. ................. 351/206 |
| 7,219,996 B2 * | 5/2007 | Ichikawa ..................... 351/206 |
| 7,275,824 B2 * | 10/2007 | Hoshino ..................... 351/206 |
| 2005/0063032 A1 | 3/2005 | Igasaki et al. .............. 359/237 |
| 2005/0231685 A1 | 10/2005 | Akita et al. .................. 351/200 |
| 2006/0087617 A1 | 4/2006 | Roorda et al. .............. 351/221 |

FOREIGN PATENT DOCUMENTS

| DE | 41 16 067 A 1 | 11/1991 |
|---|---|---|
| JP | A 06-114008 | 4/1994 |
| JP | A 2005-501587 | 1/2005 |
| WO | WO 03/036368 | 5/2003 |

\* cited by examiner

*Primary Examiner*—M. Hasan
(74) *Attorney, Agent, or Firm*—Oliff & Berridge, PLC

(57) ABSTRACT

An apparatus for observing an eye of an examinee by imaging the eye, includes an irradiation optical system; an imaging optical system; a monitor; and a display control part, wherein the imaging optical system includes a wavefront detector which receives the beam reflected by the objective part to detect wavefront aberration thereof and a wavefront compensator adapted to compensate the wavefront aberration based on a detection result of the wavefront detector, the wavefront compensator being placed within an optical path of the imaging optical system excepting a common optical path with the irradiation optical system.

6 Claims, 2 Drawing Sheets

OPHTHALMIC OBSERVATION APPARATUS

BACKGROUND OF THE INVENTION

1. Field of the Invention

The present invention relates to an ophthalmic observation apparatus for observing an eye of an examinee by imaging the eye.

2. Description of Related Art

There is an apparatus constructed to irradiate and scan a laser beam in two dimensions over an objective part to be observed such as a fundus and receives the beam reflected by the objective part by a photo-receiving element (a photo-detector) to produce an image of the objective part. The apparatus of this type can produce high resolution images as compared with a conventional fundus camera or the like. However, a further improved apparatus has been demanded to produce higher resolution images of the objective part.

BRIEF SUMMARY OF THE INVENTION

The present invention has been made in view of the above circumstances and has an object to provide an ophthalmic observation apparatus capable of producing a high-resolution image of an objective part to be observed.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an apparatus for observing an eye of an examinee by imaging the eye, comprising: an irradiation optical system including a laser source which emits a laser beam and a scanning unit which two-dimensionally scans the beam onto an objective part of the examinee's eye to be observed, the irradiation optical system being adapted to irradiate the beam to the objective part; an imaging optical system including a photo-receiving element which receives the beam reflected by the objective part; a monitor; and a display control part which produces an image of the objective part based on an output signal from the photo-receiving element, and causes the monitor to display the image; wherein the imaging optical system includes a wavefront detector which receives the beam reflected by the objective part to detect wavefront aberration thereof and a wavefront compensator adapted to compensate the wavefront aberration based on a detection result of the wavefront detector, the wavefront compensator being placed within an optical path of the imaging optical system excepting a common optical path with the irradiation optical system.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
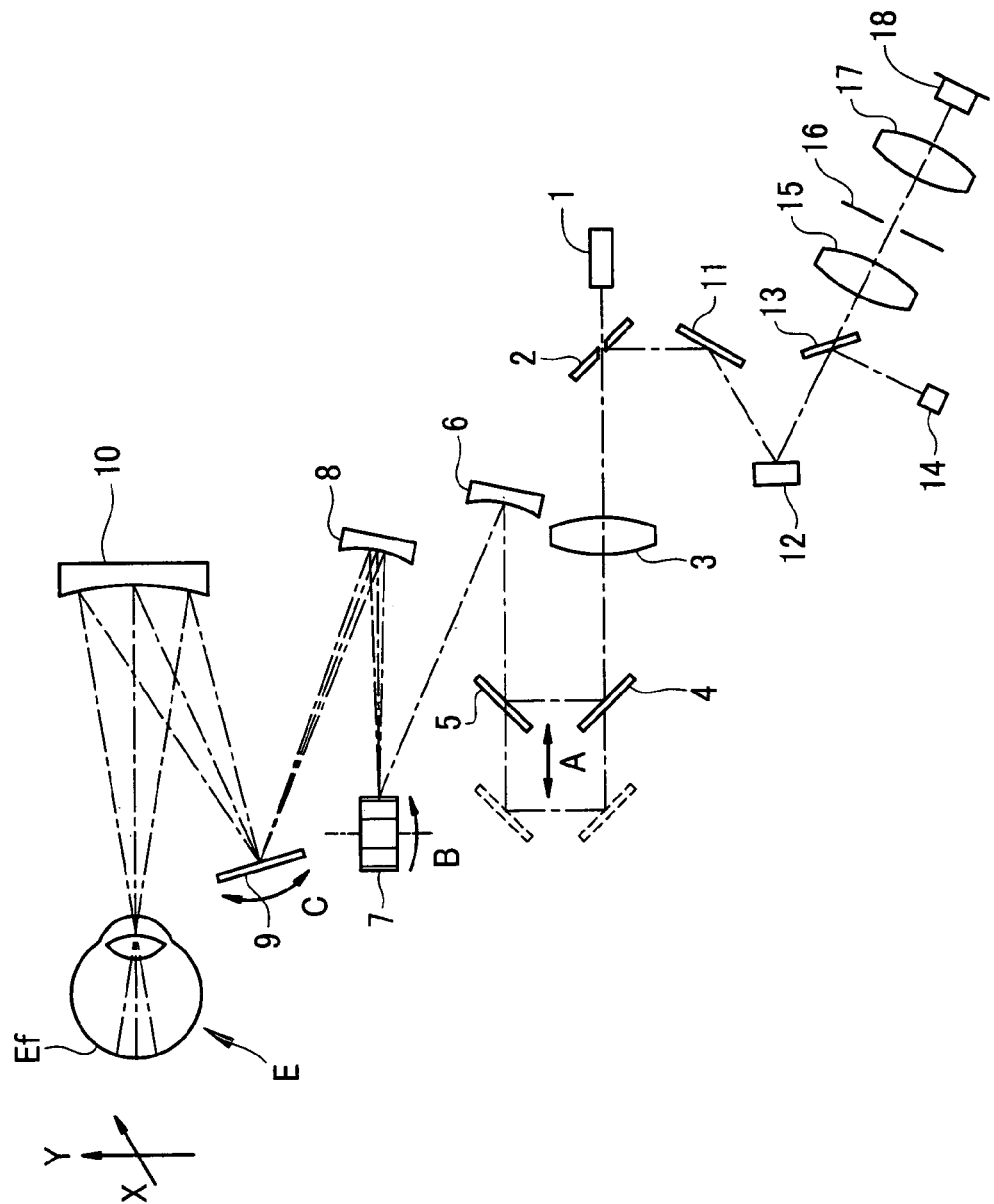
FIG. 1 is a schematic structural view of an optical system of a fundus observation apparatus in an embodiment of the present invention.

A detailed description of a preferred embodiment of the present invention will now be given referring to the accompanying drawings. FIG. 1 is a schematic structural view of an optical system of a fundus observation apparatus in the present embodiment.

A laser beam emitted from a laser source 1 passes through a center opening (hole) of a perforated mirror 2 and a lens 3 and is reflected by plane reflecting mirrors 4 and 5 and a concave reflecting mirror 6, and falls on a polygon mirror 7. The beam reflected by the polygon mirror 7 is then reflected by a concave reflecting mirror 8, and falls on a galvano-mirror 9. The beam reflected by the galvano-mirror 9 is reflected by a concave reflecting mirror 10 and is concentrated (condensed) on an objective part to be observed of a fundus Ef of an examinee's eye E. The mirrors 4 and 5 are synchronously movable in a direction indicated by an arrow A to change an optical path length of the beam for diopter correction (for focusing) of the eye E. The polygon mirror 7 is rotated in a direction indicated by an arrow B in order to scan the beam in a horizontal direction (an X-direction). The galvano-mirror 9 is swung (oscillated) in a direction indicated by an arrow C to scan the beam in a vertical direction (a Y-direction). With this structure, the beam is irradiated onto the objective part of the fundus Ef while scanning it in two dimensions (in the X- and Y-directions). These optical members constitute an irradiation optical system (a light projecting optical system).

In the present embodiment, used as the laser source 1 is a semiconductor laser source which emits an infrared laser beam of linear polarized light having a predetermined polarization direction.

The beam reflected from the objective part of the fundus Ef travels back along the irradiation optical system and is reflected by a portion surrounding the opening of the perforated mirror 2.

The beam reflected by the perforated mirror 2 is reflected by a plane reflecting mirror 11 and enters a wavefront compensator 12.

The wavefront compensator 12 is disposed within an optical path of an imaging optical system excepting a common optical path with the irradiation optical system. This makes it possible to achieve a downsized apparatus as compared with a case where the wavefront compensator 12 is disposed in the common optical path. For this wavefront compensator 12, for example, a liquid-crystal spatial phase modulator, typified by e.g. PPM (a programmable phase modulator) made by Hamamatsu Photonics K.K. is used. In the wavefront compensator 12, an aligning direction of liquid crystal molecules in a liquid crystal layer is nearly parallel to a polarization plane of the incident beam. Further, in the wavefront compensator 12, a predetermined plane, relative to which liquid crystal molecules will rotate in response to changes in applied voltage to the liquid crystal layer, is nearly parallel to a plane including an incident optical axis and a reflecting optical axis of the beam and the normal to a mirror layer of the wavefront compensator 12.

The beam is reflected by a reflecting plane of the wavefront compensator 12 in which wavefront aberration is compensated. Successively, the beam partly passes through a half mirror 13 and a lens 15 in order and then is focused on a center pinhole of a pinhole plate 16. The beam focused on the pinhole passes through a lens 17 and then is received by a photo-receiving element (a photo-detector) 18. The opening of the perforated mirror 2 is substantially conjugated with the pupil of the eye E with respect to the lens 3.

The pinhole of the pinhole plate 16 is substantially conjugated with the objective part of the fundus Ef with respect to the lens 15. These optical members constitute the imaging optical system (a photo-receiving optical system).

Further, part of the beam of which wavefront aberration has been compensated is reflected by the half mirror 13 and then enters a wavefront detector 14. The wavefront detector 14 detects the wavefront aberration to obtain information on the wavefront aberration to be compensated by the wavefront compensator 12. For this wavefront detector 14, for example, a Hartmann-Shack sensor, a wavefront curvature sensor for detecting a change in light intensity, and others are used. The reflecting plane of the wavefront compensator 12 and a light receiving plane of the wavefront detector 14 may be conjugated with the pupil of the eye E. In this case, a needful optical member has to be disposed in the imaging optical system.

In the present embodiment, used as the photo-receiving element 18 is an Avalanche Photodiode (APD).

In the present embodiment, the laser source 1 is placed so that the beam of the linear polarized light enters the wavefront compensator 12 as a P-polarized beam, but not limited thereto. A ½ wave plate for changing a polarization direction of P waves may be placed in the optical path of the imaging optical system between the perforated mirror 2 and the wavefront compensator 12. Such ½ wave plate is rotated to provide the polarization direction of appropriately producing an image of the objective part (the polarization direction of efficiently reflecting the beam to the wavefront compensator 12). This ½ wave plate is preferably located within the optical path of the imaging optical system excepting the common optical path with the irradiation optical system.

Figure 2:
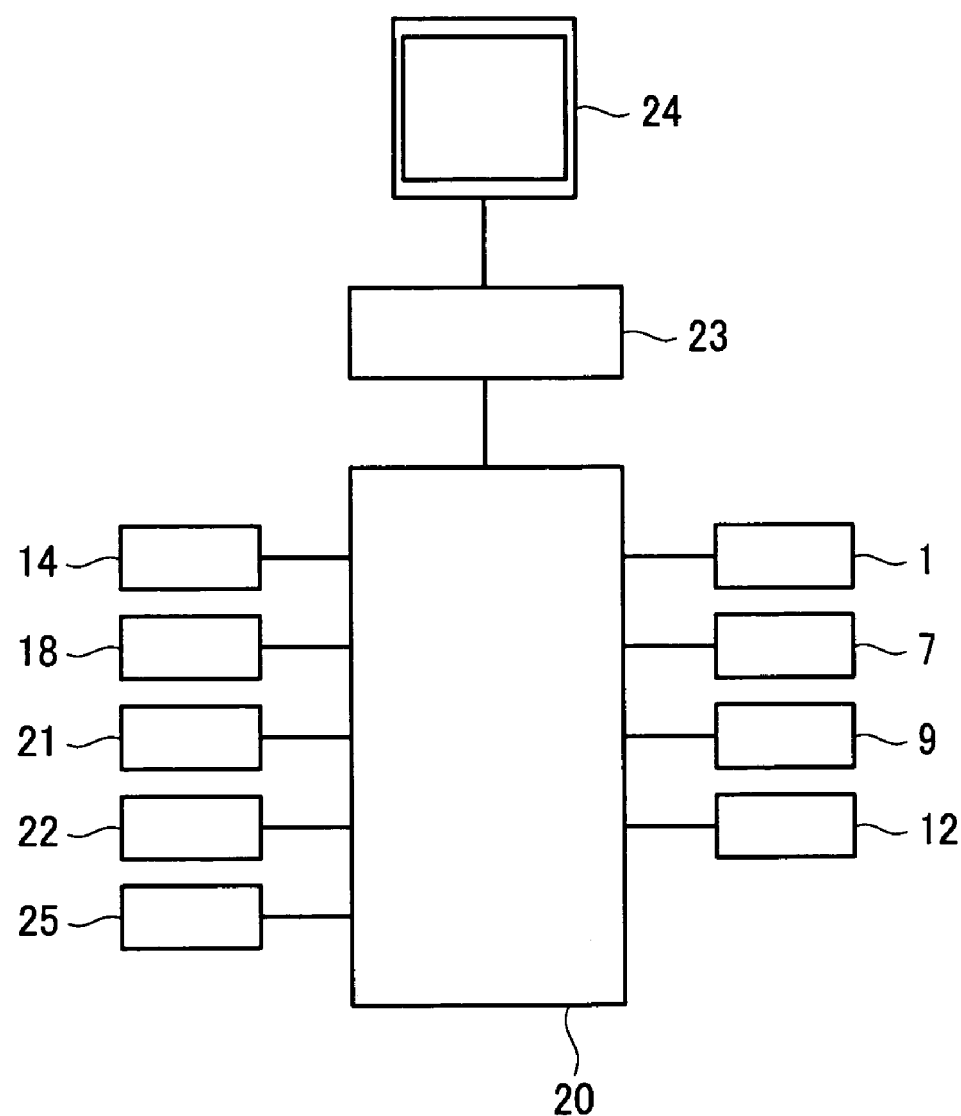
FIG. 2 is a schematic block diagram of a control system of the apparatus.

FIG. 2 is a schematic block diagram of a control system of the apparatus. Connected to a control part 20 which controls the entire apparatus are the laser source 1, the polygon mirror 7, the galvano-mirror 9, the wavefront compensator 12, the wavefront detector 14, the photo-receiving element 18, a moving unit 21 for moving the mirrors 4 and 5, an input part 22, an image processing part (a display control part) 23, a monitor 24, a memory part 25, and others. The input part 22 is provided with switches and others for inputting data on refractive power of the eye E in order to correct diopter. The image processing part 23 produces an image based on an output signal from the photo-receiving element 18, and causes the monitor 24 to display the image. The memory part 25 stores various setting information, captured images, etc.

Operations of the apparatus constructed as above will be described below.

An examiner inputs data on the refractive power of the eye E, which is a previously measured result through an eye refractive power measurement apparatus or the like, with the input part 22. The control part 20 stores the inputted refractive power data in the memory part 25 and also causes the moving unit 21 to move the mirrors 4 and 5 based on the data, thus correcting the diopter. Successively, the examiner manipulates a joystick or the like not shown to move the apparatus after the diopter correction to make alignment with respect to the eye E so that the image of the objective part of the fundus Ef appears on the monitor 24.

The beam irradiated to and reflected by the objective part of the fundus Ef is reflected by the reflecting plane of the wavefront compensator 12. The beam reflected by the wavefront compensator 12 is partially reflected by the half mirror 13 and received by the wavefront detector 14. The control part 20 performs a Fourier transform of an optical distribution (a photo-receiving signal) detected by the wavefront detector 14 and, based on the result, dynamically controls the phase of pupil function of a compensating optical system. In the present embodiment, a liquid crystal layer of the wavefront compensator 12 is used for phase modulation of the pupil function. The aligning direction of liquid crystal molecules in the liquid crystal layer is changed by voltage control, thereby controlling a phase distribution so that a spreading range of a diffraction pattern of the beam reflected by the objective part of the fundus Ef is reduced to a minimum. With the above structure, the beam reflected by the wavefront compensator 12 whereby the wavefront aberration is compensated is received by the photo-receiving element 18.

The image processing part 23 produces an image of the objective part based on the output signal from the photo-receiving element 18, and causes the monitor 24 to display that image. In the present embodiment, because the objective part of the fundus Ef and the pinhole of the pinhole plate 16 are conjugated with each other, only the beam from the objective part of the fundus Ef is allowed to pass through the pinhole and be received by the photo-receiving element 18. Accordingly, a clear image of the objective part can be obtained. For ensuring an adequate light quantity of the beam or others, an additional system for changing the diameter of the pinhole of the pinhole plate 16 may be provided.

In the above embodiment, a reflection-type wavefront compensator is used as the wavefront compensator 12, but other types may also be adopted. A transmission-type wavefront compensator which allows the beam reflected by the objective part to pass therethrough to thereby compensate wavefront aberration may be adopted.

As the wavefront compensator 12, furthermore, any well known device may also be used; for example, micro-electro-machined (MEMs) membrance mirrors, MEMs segmented mirrors, bimorph deformable mirrors, electrostatic membrance deformable mirrors. The liquid crystal spatial phase modulator is easy to control and capable of compensating wavefront aberration with high accuracy.

Although the above embodiment was explained using the fundus observation apparatus, the present invention may also be applied to an apparatus for imaging and observing an anterior segment of an eye and so on.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An apparatus for observing an eye of an examinee by imaging the eye, comprising:

an irradiation optical system including a laser source which emits a laser beam and a scanning unit which two-dimensionally scans the beam onto an objective part of the examinee's eye to be observed, the irradiation optical system being adapted to irradiate the beam to the objective part;

an imaging optical system including a photo-receiving element which receives the beam reflected by the objective part;

a monitor; and a display control part which produces an image of the objective part based on an output signal from the photo-receiving element, and causes the monitor to display the image;

wherein the imaging optical system includes a wavefront detector which receives the beam reflected by the objective part to detect wavefront aberration thereof and a wavefront compensator adapted to compensate the wavefront aberration based on a detection result of the wavefront detector, the wavefront compensator being placed within an optical path of the imaging optical system excepting a common optical path with the irradiation optical system.

2. The apparatus according to claim 1, wherein the wavefront compensator is a liquid crystal spatial phase modulator.

3. The apparatus according to claim 1, wherein the wavefront compensator is a reflection-type wavefront compensator.

4. The apparatus according to claim 1, wherein the wavefront compensator is a transmission-type wavefront compensator.

5. The apparatus according to claim 1, wherein the wavefront detector is either a Hartmann-Shack sensor or a wavefront curvature sensor.

6. The apparatus according to claim 1, wherein the laser source is placed so that the beam of linear polarized light enters the wavefront compensator as a P-polarized beam.

* * * * *